United States Patent [19]

Mitsuda et al.

[11] Patent Number: 5,079,161
[45] Date of Patent: Jan. 7, 1992

[54] METHOD AND APPARATUS FOR CELL CULTURE WITH IMMOBILIZING CARRIERS

[75] Inventors: Shinjiro Mitsuda, Hasuda; Yoshiaki Matsuda, Sashima; Naoki Kobayashi, Ishibashi; Eitaro Kumazawa, Tochigi; Hideo Sakuma, Chiba, all of Japan

[73] Assignee: Snow Brand Milk Products Co., Ltd., Hokkaido, Japan

[21] Appl. No.: 370,028

[22] Filed: Jun. 22, 1989

[30] Foreign Application Priority Data

Jun. 27, 1988 [JP] Japan ............................. 63-158714
Jun. 27, 1988 [JP] Japan ............................. 63-158715

[51] Int. Cl.$^5$ .................. C12N 5/00; C12N 11/14; C12N 3/00; C12N 11/00
[52] U.S. Cl. ..................... 435/240.23; 435/174; 435/176; 435/240.24; 435/284; 435/285; 435/286; 435/288; 435/819
[58] Field of Search ............ 435/174, 176, 240.23, 435/240.24, 284, 285, 286, 288, 819

[56] References Cited

PUBLICATIONS

Pharmacia Fine Chemicals, Microcarrier Cell Culture Principles and Methods, 1985, pp. 13-16, 24,25,34,35,44,45,49,50,55-6174 and 75.

*Primary Examiner*—David M. Naff
*Attorney, Agent, or Firm*—Griffin, Branigan & Butler

[57] ABSTRACT

Cell cultivation is carried out by proliferating cells in a small preliminary culture tank containing immobilizing carriers, stripping proliferated cells from the carriers, forming a cell suspension of the stripped cells in culture medium in an intermediate reservoir, intermittently transferring the suspension into a main culture tank containing ceramic immobilizing carriers and further culturing the cells. The main culture tank has an inversed funnel-shaped inlet above the carriers with a perforated plate attached to the bottom of the inlet for uniform distribution of cell suspension from above the carriers, and a plate in the form of a net under the carriers on a perforated plate for uniform distribution of cell suspension from beneath the carriers. The main tank additionally has a lid detachably carrying the inversed funnel-shaped inlet an intermediate drum-shaped portion from which the lid is detachable and a lower portion detachably carrying the plate in the form of a net and being detachable from the drum-shaped portion. The lower portion is held on or separated from the drum-shaped portion by means of a link mechanism and a cylinder capable of lowering the lower portion to separate it from the drum-shaped portion.

10 Claims, 5 Drawing Sheets

METHOD AND APPARATUS FOR CELL CULTURE WITH IMMOBILIZING CARRIERS

BACKGROUND OF THE INVENTION

The present invention relates to a method and an apparatus for efficient proliferation and culture of adhesive cells followed by transfer of said cells into a mass culture tank so as to produce a physiologically active substance.

Culture of adhesive cells has conventionally been performed by use of various culture system as follow:

(a) So-called liquid tight system generally comprising a plurality of plates arranged in a parallel manner within a container in order to obtain a sufficiently large surface for cell adhesion. Upon completion of said cell adhesion onto the plates, a quantity of culture fluid is circulated in the container under control of pH and DO (dissolved oxygen). The so-called rotary system generally comprising a plurality of discs or the like also arranged in parallel within a cylinder set upright to achieve the cell adhesion onto the discs and then laid down to be rotated.

(b) A system comprising scrolled plastic film charged within a cylinder, wherein cell culture is performed in the same manner as the so-called roller culture. Then a quantity of culture fluid is circulated in the cylinder, set upright, for example, by air supplied into the cylinder.

(c) The multitray system of box-nest construction similar to the system set forth above in (a) except that there is gaseous phase and the culture can be stationary as achieved in roller botter, without the requirement for the culture fluid circulation.

(d) The plastic bag system comprising an oxygen or carbon dioxide-permeable plastic bag rolled up like the fire hose through which a quantity of culture fluid flows. This system facilitates the control of DO and pH.

(e) The hollow fiber system comprising hollow fibers as usually used for artificial kidney dialysis, wherein adhesion and proliferation of cells occur on the exterior side while nutrient supply occurs from the interior side of each hollow fiber, i.e., from the near side of the cell layer.

(f) The glass beads filled column system in which adhesion and proliferation of cells occur on the surfaces of glass beads charged within a container under circulation of a culture fluid having pH and DO previously adjusted.

(g) The microcarrier system utilizing, instead of said glass beads, minute beads of such specific gravity that these minute beads float in culture fluid under a gentle agitation in order of 20 to 40 r.p.m. and the culture, as well as proliferation of cells occur on their surfaces.

The systems (a) through (d) are exclusively for the batch production and the number of cells which can be cultivated for each process results in a poor yield of the target substance.

The systems (e) through (f), of the continuous culture medium circulation type, are also restricted in the number of cells which can be cultivated and is not suitable for mass culture.

Presently, the mass culture has mostly relied on the microcarrier system set forth above in (g) and such system having a capacity of 8000 is known.

One example of the microcarrier system is disclosed in Japanese Disclosure Gazette No. 0982-5670, which aims at efficient cell culture within a culture tank containing a cylindrical member set upright therein, by providing said cylindrical member therein with deflectors and connecting said cylindrical member with a culture fluid outlet conduit so that a desired quantity of culture fluid may be stably circulated for a long period. As a similar example, Japanese Disclosure Gazette No. 1985-168379 discloses a cell cultivating apparatus having a unit comprising a plurality of hollow fibers each having a wall-membrane which is cell-impermeable but nutrient-permeable, said unit being provided at opposite ends or one end with an inlet and an outlet for cell culture fluid so that high mass and high density culture can be achieved by suspension culture. As still another example, Disclosure Gazette No. 1985-259179 discloses a similar mass and high density cell culture tank of the suspension type which is provided at the top with an inlet for fresh culture fluid, at the bottom with an outlet for used culture fluid, and adjacent the top with an impeller.

The above-mentioned systems of the prior art are disadvantageous in that the cultivating capacity can be improved only by making the culture tank volume correspondingly larger and proliferation of cells from the initial stage in such larger culture tank would not only encounter additional problems as those in circulation and control of correspondingly increased culture fluid but also take a longer time period.

Particularly when it is desired to produce physiologically active substance by cell culture, the culture medium for cell proliferation has ingredients different from those for cell culture and the former becomes wasteful especially in the larger culture tank.

Accordingly, the method according to the present invention, in view of such problems encountered by the microcarrier system of well known art, intends to achieve an efficient cell culture by performing the initial cell proliferation and the subsequent cell culture for production of the physiologically active substance in different tanks.

For the cells which are readily subject to damage due to the shearing force and have relatively low colony formation efficiency it is very difficult to perform the microcarrier culture. To reduce the effect of said shearing force, the method is preferably, one in which the cells themselves are adhesively fixed onto particular material having a larger surface area in the stationary culture method and the culture medium is circulated, therethrough.

The previously mentioned hollow fiber system is one embodiment of such method. Specifically, the culture medium is continuously circulated not only through the interior but also along the exterior surface of the hollow fiber on which the adhesive cells are to be prolifirated so that the nutrient and metabolism product are efficiently moved between the interior and the exterior of the fiber, enabling the cells to be cultivated at a high density.

However, this system unacceptably complicates the apparatus and has not been commercially adopted for mass production.

Japanese Disclosure Gazette No. 1984-154984 discloses a simplified hollow fiber system in which the cells are proliferated, cultivated on ceramic matrix and the culture fluid is continuously circulated.

According to this prior art, alumina, silica, titanium, zircon or the like or combination thereof is sistered to form porous ceramic carrier which is a cylindrical monolithic carrier having at least about 20 throughholes extending in parallel to one another per square inch of cross-section. However, this system is inconvenient in that the carrier is readily clogged as it is continuously used.

As will be appreciated from the foregoing description, all of the conventional system are disadvantageous for mass production in commercial scale. To over come such problems, the inventors disclosed a solution in Japanese Disclosure Gazette No. 1987-236480. This solution is a method comprising steps of providing ceramic particles consisting for the most part of alumina suitable for all adhesion and having an approximately uniform size of 5 to 9 meshes, supplying culture fluid into a column filled with said ceramic particles, exchanging the quantity of aged culture fluid, after movement through the first half of the column, due to proliferation of cells with quantity of fresh culture fluid at an intermediate level of column, and removal of said aged culture is further continued through the second half of the column.

This method is characterized by that the effort of culture fluid to the cells is relatively uniform, the cells are free from the damage due to a shearing force and the carrier facilitates the cell adhesion, and thus the method is suitable for mass culture of adhesive cells.

Nevertheless, there still remains an important problem that, when cultivation is performed within a column or tank filled with granular sedimentary immobilizing carrier whether it is ceramic or not, filling and removal of the immobilizing carrier should not prevent the cells from achieving their uniform adhesion onto said immobilizing carrier.

With this method, however, a quantity of cell suspension supplied to the immobilizing carrier stack is initially apt to stagnate at the cell suspension supply side on the stack surface and at the area adjacent the supply pipe. This is inconvenient in that a long time is taken before the cells can be proliferated through out the whole immobilized carrier stack.

The cell culture apparatus of the present invention intends to solve such problem.

SUMMARY OF THE INVENTION

An object of this invention is to provide a method for efficient cell cultivating method adapted to perform initial cell proliferation and subsequent cell culture for production of a target substance in different tanks.

This object is achieved, in accordance with the present invention, by a method for cell culture comprising steps of: proliferating adhesive cells in a preliminary culture tank of smaller size; stripping off the cells thus proliferated from immobilizing carriers and then mixing these cells with a part of culture medium which has been adjusted in an intermediate reservoir to obtain a quantity of cell suspension; collecting the cell suspension thus obtained into said intermediate reservoir to be stored therein; transferring, as occasion demands, said cell suspension stored in said reservoir, after the cell distribution therein has been uniformalized, into a main culture tank filled with immobilizing carriers containing ceramic material as a main ingredient so that the cells adhere to said immobilizing carriers and are further cultivated and finally producing physiologically active substance on a culture ground of this purpose.

This method is effectively carried out by a cell culture apparatus comprising a preliminary culture tank of a smaller size, a main culture tank filled with immobilizing carriers containing ceramic material as a principal ingredient, and an intermediate reservoir interposed between said preliminary culture tank and said main culture tank. After cell proliferation, a quantity of cell suspension is supplied to said main culture tank filled with immobilizing carriers containing ceramic material as the principal ingredient.

Efficient cell adhesion onto the immobilizing carriers is accomplished by providing the above-mentioned cell culture apparatus with a separate tank. The cells profilerated in the small preliminary culture tank are stripped off from the immobilizing carriers to prepare cell suspension. The latter is transferred to the main culture tank filled with immobilizing carriers. The cell suspension is supplied to said main culture tank from top and bottom thereof so as to uniformalize cell adhesion onto said immobilizing carriers. This also serves to adjust the nutrient and gas content in the culture fluid, as well as to control circulation of said culture fluid within said main tank filled with the immobilizing carriers principally made of ceramic material.

It should be understood that the microcarrier type culture tank is most preferable a small size preliminary culture tank, since cells, as many as possible, will be supplied to the subsequent mass culture tank.

The method and the apparatus for cell culture according to the present invention provide a unique effect as will be described hereinafter.

Generally, proliferation as well as culture can be efficiently achieved by proliferating cells to be used in a next process of production in the preliminary culture tank while the target substance is produced, because the initial cell proliferation and said production of the target substance are performed in the different culture tanks.

More specifically, it is possible to confirm the number of cells so that the cell proliferation in the preliminary culture tank can be efficiently achieved. The proliferation medium can be effectively supplied for the minimum time and thus the change over from said proliferation medium to the culture fluid for production of the physiologically active substance is shortened, which results in shortening of the cultivating time.

The efficient cell culture as mentioned above has various merits in view of a fact that, in general, the life of a cell is relatively short.

In addition, supplying the cell suspension to the immobilizing carriers from top and bottom of the culture tank enables the cell adhesion onto said immobilizing carriers to be uniformly and effectively accomplished.

Another object of the present invention is to provide a culture apparatus adapted to uniformly supply the cell suspension to the immobilizing carriers and to facilitate charging as well as removal of said immobilizing carriers.

Uniform supply of the cell suspension to the immobilizing carriers set forth above as one factor of this object is achieved, in accordance with the present invention, by a culture apparatus filled with segmentary immobilizing carriers for adhesive cells and aiming at production of a target substance. The culture apparatus comprising an inversed funnel-shaped inlet located above the immobilizing carriers filling the apparatus and having a perforated bottom plate for uniform distribution of a quantity of cell suspension supplied from above to said immobilizing carriers. A netty plate located under the immobilizing carriers holds said immobilizing carriers, and another perforated plate is also located under the immobilizing carriers for uniform distribution of a quantity of cell suspension supplied from the bottom to said immobilizing carriers.

To facilitate filling and removal of the immobilizing carriers, i.e., to achieve another requirement of the above-mentioned object, the present invention provides an apparatus comprising a cover portion adapted for detachably carrying the inversed funnel-sharped fluid inlet having the perforated bottom plate for uniform distribution of the quantity of cell suspension supplied from above to the immobilizing carriers filling the apparatus. A drum portion is fixed to a stand and a bottom portion is adapted for detachably carrying the netty plate to hold the immobilizing carriers from the underside and the perforated plate for uniform distribution of the quantity of cell suspension supplied from bottom portions.

The culture apparatus of the present invention provides an effect as follows:

Supply of cell suspension to the immobilizing carriers occurs from both top and bottom of the apparatus filled with said carriers so that the quantity of said cell suspension supplied from the top is uniformly supplied through the perforated plate as a part of the inverted funnel-shaped inlet and the quantity of cell suspension supplied from the bottom is uniformly distributed through the lower perforated plate and then the netty plate supports the immobilizing carriers. Thus, cells uniformly adhere onto the immobilizing carriers.

Furthermore, the bottom portion of the culture apparatus can be separated from and connected to the cover and drum portions of the culture apparatus by means of a linkage and a cylinder so as to facilitate charging and removal of the immobilizing carriers and thereby shorten the time taken for such operation.

Additionally, dividable construction of the culture apparatus facilitates manual washing and checking.

Thus, both washing and checking are further easier than those usually performed for the conventional culture tank of one-piece type and the culture apparatus constructed according to the present invention is novel one as such apparatus utilizing segmentary immobilizing carriers.

BRIEF DESCRIPTION OF THE DRAWINGS

These and other objects as well as advantages of the present invention will become clear by the following description of preferred embodiments of the present invention with reference to the accompanying drawing, wherein.

DETAILED DESCRIPTION OF THE INVENTION

Figure 1:
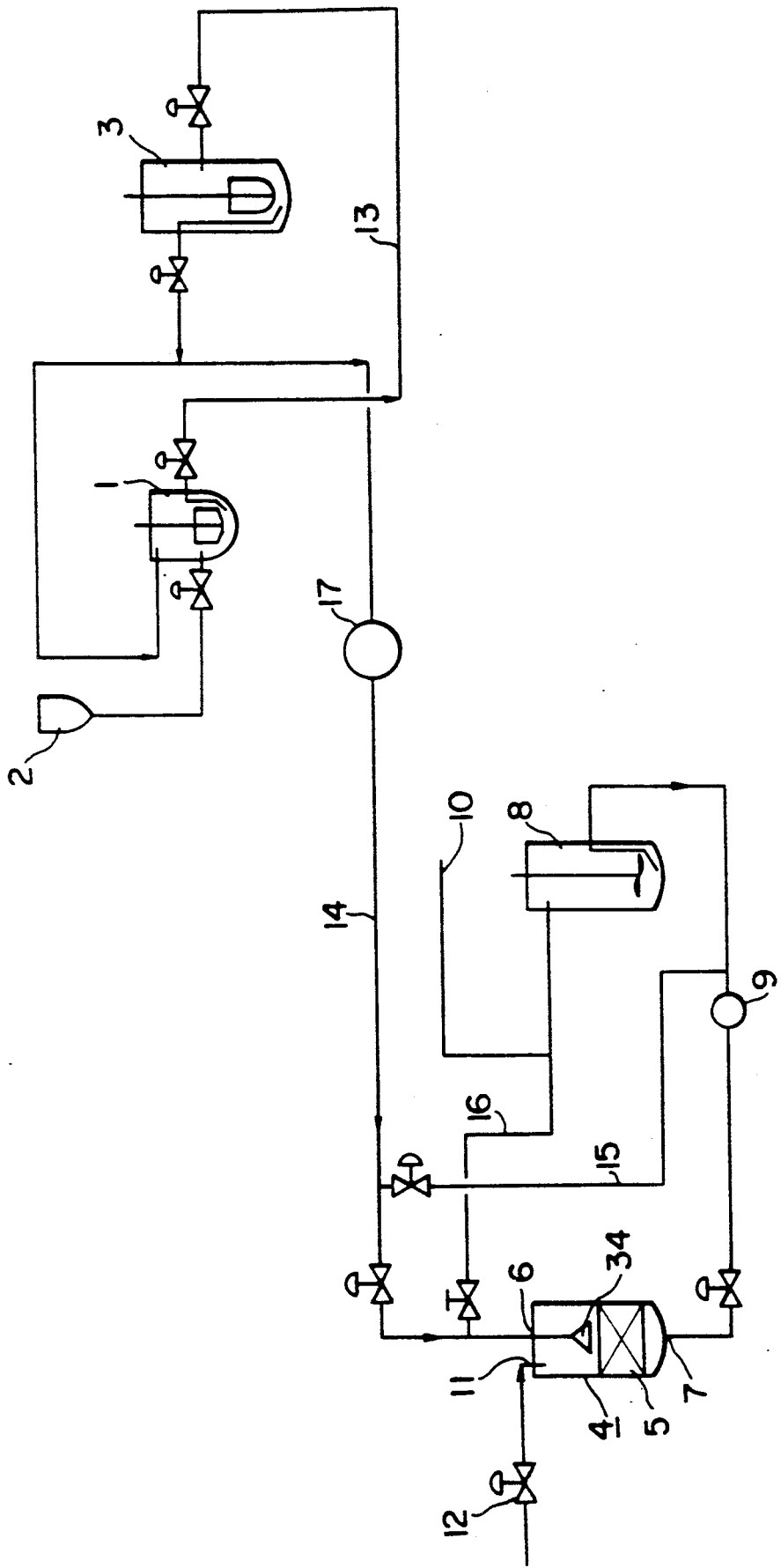
FIG. 1 is a flow chart schematically illustrating the method for cell culture according to the present invention.

First, the method for cell culture according to the present invention will be described in reference with FIG. 1.

Reference numeral 1 designates a small sized culture tank used to perform the method of the present invention and, specifically, a microcarrier culture tank is used here as this small sized culture tank, within which proliferation of adhesive cells occurs according to the microcarrier culture process. It should be understood that, although said microcarrier culture tank used in the inventive method, the culture tanks of other types may be effectively employed.

Reference numeral 2 designates a nutrient reservoir to supply said microcarrier culture tank 1 with nutrient.

The cells initially proliferated within the microcarrier culture tank 1 are stripped off by the well known technique from the microcarriers to obtain a suspension, which is then transferred via a conduit 13 into an intermediate reservoir 3. The cell suspension is temporarily stored in this intermediate reservoir 3 to uniformize cell distribution.

Reference numeral 4 designates a mass culture tank filled with ceramic carriers. A quantity of cell suspension is supplied by a pump 17 from said cell suspension reservoir 3 through a conduit 14 and then through an upper conduit 6 extending through the top of the culture tank 4 into a layered ceramic 5 while another quantity of cell suspension is supplied through a conduit 15A and 15B (see FIG. 2) branched from the conduit 14 and then through a lower conduit 7 connected to the bottom of the culture tank 4 into said layered ceramic 5.

Cell suspension is supplied in the two-way fashion to the culture tank in the manner as has been mentioned above and thereby uniform adhesion of the cells onto the immobilizing ceramic carriers is achieved.

The quantity of cell suspension to be supplied to the mass culture tank in the two-way fashion must be previously adjusted to the optimum quantity at a stage of culture medium adjustment within the intermediate reservoir, since it would be impossible to achieve uniform adhesion of cell onto the ceramic carriers if said quantity of cell suspension is excessively larger than the quantity of the ceramic carriers within the mass culture tank and effective utilization of whole the ceramic carriers would be impossible if said quantity of cell suspension is smaller thah the quarity of the ceramic carriers.

Reference numeral 8 designates a culture fluid adjusting tank adapted to effect the culture fluid circulation within the culture tank 4 and to control nutrient and gaseous content of the culture fluid. The culture tank 4 is supplied from its top and bottom with the cell suspension from the intermediate reservoir 3 so that the cells uniformly adhere onto the individual ceramic carriers forming the layered ceramic 5 and then the culture tank 4 is supplied with culture fluid for cell proliferation under action of a pump 9 from the culture fluid adjusting tank 8. Referring to the method of efficient proliferation, channeling can be prevented where the carries are filled, by having upward and downward circulation alternately. Downward circulation occurs in such a manner that said culture fluid is pumped by pump 9 from the culture fluid adjusting tank 8 into the culture tank 4 via conduits 18, 48, 15A, 14, 6 and the inverse funnel-like inlet 34, and returned to said tank 8 via conduits 7, 46, and 16B. Upward circulation occurs in such a manner that said culture fluid is pumped by pump 9 from the culture fluid adjusting tank 8 and into said culture tank 4 via conducts 18, 7 and then though the inverse funnel-like inlet 34, and returned to said tank 8 via conduits 6, 14, 16A, and 16B.

These upward and downward circulation occurs alternately automatically every certain minutes and the uniform distribution and proliferation of the cell without causing channeling will be realized.

Further, an air pressure supplied from an air inlet 11 into the culture tank 4 under control of an air valve 12 operatively associated with a level control rod so as to maintain a fluid level within the culture tank adjacent the inverse funnel-like inlet 34.

Furthermore, instead of said alternate circulation, either the upward or downward circulation can be used alone.

After the cells have been proliferated to a predetermined number under circulation of said culture fluid for proliferation, change-over occurs from this culture fluid for proliferation to the culture fluid for production of a physiologically active substance is supplied from a reservoir not shown. Now the culture fluid for production of the physiologically active substance supplied into the culture tank 4 and, after the physiologically active substance has been produced, this culture fluid containing therein said substance is recovered through line 10 into a column for elution of the physiologically active substance.

Upon completion of the recovery, the cell suspension is supplied again from the intermediate reservoir 3 into the culture tank 4 and the cell culture is repeated.

In this manner, the initial cell proliferation occurs within the microcarrier culture tank 1 while the final cell culture for production of the physiologically active substance occurs within the culture tank 4. Thus, the proliferation and the culture are carried out within the different culture tanks being in communication with each other via the intermediate reservoir.

As has previously been described, cell stripping in the small sized culture tank may be performed by any suitable conventional techniques. One of these useful techniques will be described in detail. Upon completion of the cell proliferation, circulation of culture fluid is stopped. Then, the entire quantity of culture fluid is removed out from the small sized culture tank, and washed with phosphate buffer saline (PBS), followed by stripping of the cells effected by supplying a suitable quantity of trypsin or collagenase. It should be noted here that contact of trypsin or collagenase with the cells for a long time would destroy the cells. To avoid this, a quantity of culture fluid containing trypsin inhibitor is supplied thereto in order to devitalize said trypsin or collagenase and thereby a quantity of cell suspension in which the cells float. If the culture is not serumless culture, said trypsin inhibitor may be substituted by serum containing culture fluid, because serum intrinsically contains therein said trypsin inhibitor.

In view of a fact that the cells are apt to be deactivated and to stick together, when the cells are left in floating condition for a long time, the cell suspension must be transferred to the immobilizing carriers as soon as possible. Namely, storage of the suspension in the intermediate reservoir is a temporary storage for adjustment.

Said intermediate reservoir 3 has an additional important function as will be described below. During the cell proliferation within the small sized culture tank 1, the intermediate reservoir 3 serves for circulation and adjustment of the culture fluid and, upon completion of the cell proliferation and once the circulation has been stopped, the reservoir serves to adjust the quantity of culture fluid to be supplied to the mass culture tank 4 for the subsequent process. The quantity of culture fluid thus adjusted is now partially supplied to the small sized culture tank, in which removal of the culture fluid, washing and stripping of the cells have already been completed, to obtain a quantity of cell suspension which is, in turn, collected into the intermediate reservoir where a quantity of uniform and adjusted cell suspension is necessary to be supplied to the subsequent mass culture tank. The intermediated reservoir is essential for such process.

The respective culture tanks as have been mentioned above require the associated adjusting tanks in order to adjust pH, temperature and nutrient properly during circulation of culture fluid, and nutrient occurs form a reservoir not shown.

Now the apparatus for cell culture constructed according to the present invention will be discussed by way of example. The apparatus of the invention has been developed by overcoming the disadvantages of the microcarrier type cell cultivating apparatus and comprises a cell culture apparatus filled with carriers adapted to immobilize sedimentary adhesive cells. This cell culture apparatus is particularly suitable as the culture tank for production of physiologically active substance, which is provided separately from the small sized preliminary culture tank for the initial cell proliferation in the method for cell culture as has been mentioned above and accordingly the apparatus of the invention will be described in connection with a specific embodiment constructed as such culture tank. However, application of the inventive apparatus is not limited to such culture tank.

Figure 2:
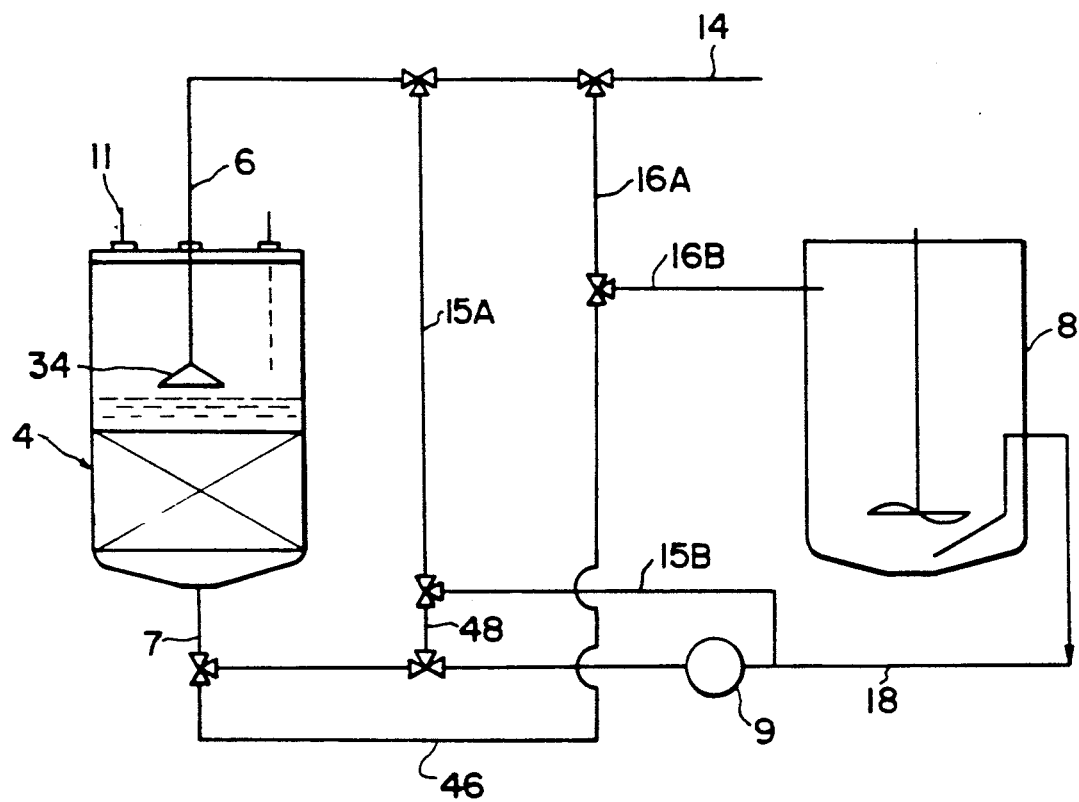
FIG. 2 is a flow chart illustrating a manner in which culture fluid for cell proliferation supplied to the culture apparatus of the present invention is circulation.

FIG. 2 schematically illustrates an embodiment of the culture apparatus according to this invention.

Figure 3:
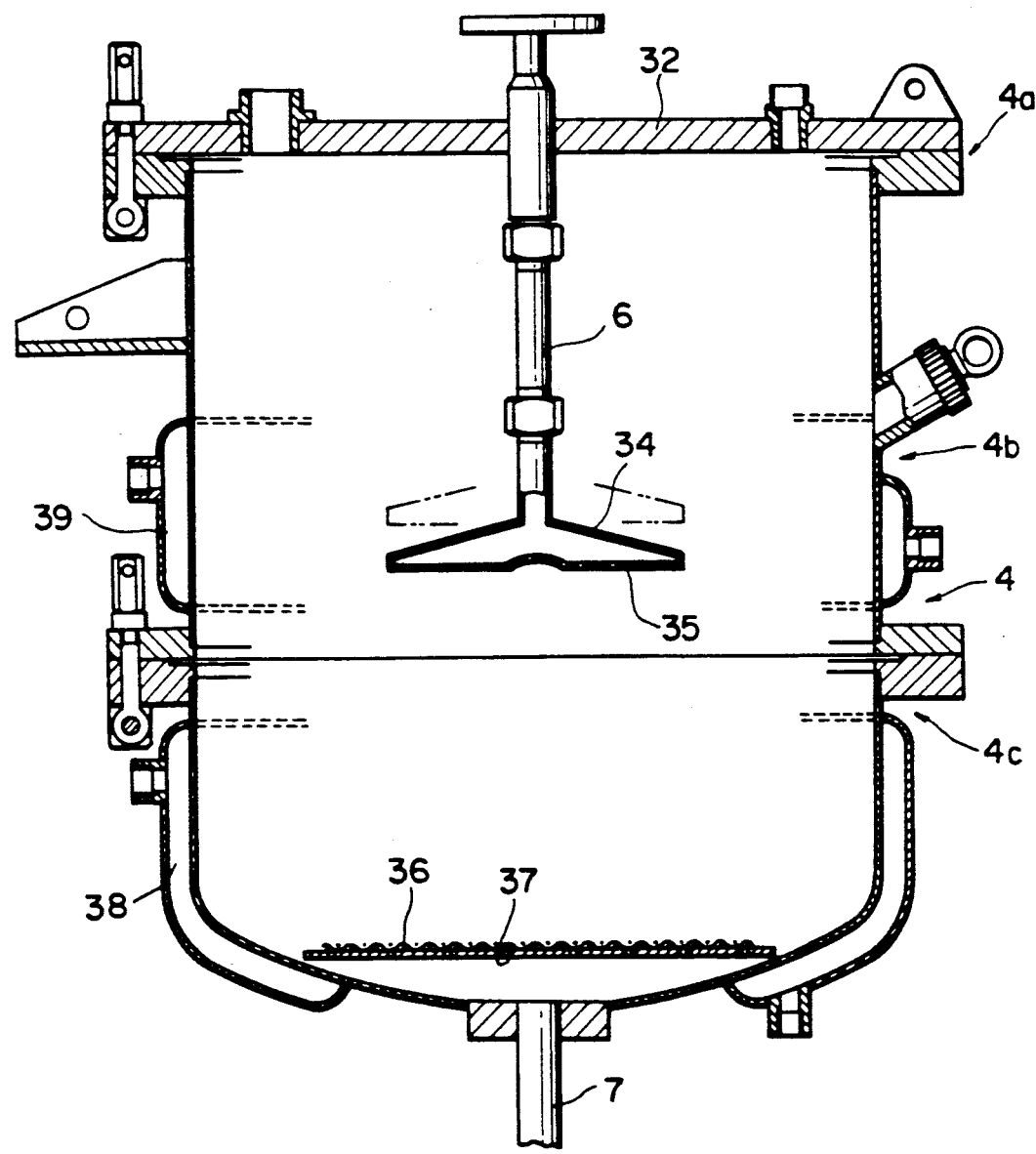
FIG. 3 is a sectional view showing the culture apparatus of the present invention.

Reference numeral 4 designates a mass culture tank filled with ceramic carriers. A conduit 6 extends from a conduit 14 for supply of cell suspension. As shown by FIG. 3, the conduit 6 is detachably mounted in a cover 32 of the culture tank 4 for supply of cell suspension and its front end terminates in an inversed funnel-shaped inlet 34 and a bottom of the inversed funnel-shaped inlet 34 is defined by perforated plate 35 adapted for uniformly supplying cell suspension to the top of immobilizing carriers.

The culture tank 4 is connected to a culture fluid adjusting tank 8 by conduits 16A, 16B, 18 so that a pump 9 disposed in the conduit 18 causes a quantity of culture fluid to circulate. The conduit 18 is connected to an inlet conduit 7 for the culture tank 4 while the conduits 16A and 16B is connected to the conduit 6 associated with the inversed funnel-shaped inlet 34 via a switchable value. Thus, a predetermined quantity of culture fluid is pumped into the culture tank 4 by said pump 9. In above-mentioned upward circulation, culture fluid is returned from the inversed funnel-shaped inlet 34 to the culture fluid adjusting tank 8 through the conduits 6, 14, 16A, 16B when the pump 9 is switched between ON and OFF by means of a fluid level control rod or when germ-free air is introduced through an inlet 11 into the culture tank 4 for pressurizing. In this manner, the fluid level is always adjusted in the proximity of the inversed funnel-shaped inlet 34.

Another embodiment of the culture tank 4 will be discussed in reference with FIG. 3. This culture tank 4 consists of an upper flange-like portion 4a, an intermediate drum-like portion 4b and a lower portion 4c which are separable from one another. The flange-like portion 4a is covered by a lid 32. The supply conduit 6 extends downwardly to the inversed funnel-shaped inlet 34 having a bottom covered by the perforated plate 35. The culture tank 4 is further provided across the lower portion with a netty plate 36 adapted to the immobilizing carriers and a perforated plate 37 directly underlying said netty plate 36. The netty plate 36 and perforated plate 37 are fixed by clamping bolts across the lower portion of the culture tank 4.

The conduit 7 is connected to the lower end of the culture tank 4. Reference numerals 38, 39 designate cooling jackets for the lower portion 4c and the drum-like portion 4b, respectively, of the culture tank 4.

It will be described how to use the culture tank 4 of the present invention particularly for production of physiologically active substance.

First of all, ceramic carriers are filled in said culture tank 4 and sterilized therein. Then, a quantity of cell suspension containing adhesive cells floating therein is supplied to the culture tank 4 through the conduit 14 and then through the conduit 6 which opens into the top of the tank 4 while another quantity of cell suspension is supplied to the culture tank 4 through the conduit 15A, 15B branched from the conduit 14 and then the inlet conduit 7 which opens into the bottom of the tank 4.

The conduit 6 terminates in the inversed funnel-shaped inlet 34 having its bottom defined by the perforated plate 35, so that the quantity of cell suspension is uniformly supplied from above into the culture tank 4 and the other quantity of cell suspension also is uniformly supplied from below into the culture tank 4 under the effect of the perforated plate 37 and the netty plate 36.

Thus, after the culture tank 4 has been supplied from top and bottom with cell suspension and the cells have uniformly adhered onto ceramic carriers, a quantity of culture fluid for cell proliferation is circulated by the pump 9 from the culture fluid adjusting tank 9 through the conduits 18, 16B, 16A for the purpose of cell proliferation. Upon adequate proliferation, culture fluid is changed over from that for cell proliferation to that for production of physiologically active substance coming from a reservoir not shown and thereby a target substance is produced.

The culture fluid adjusting tank 8 functions to adjust various factors such as pH, temperature, gaseous content and nutrient content of culture fluid.

Figure 4A:
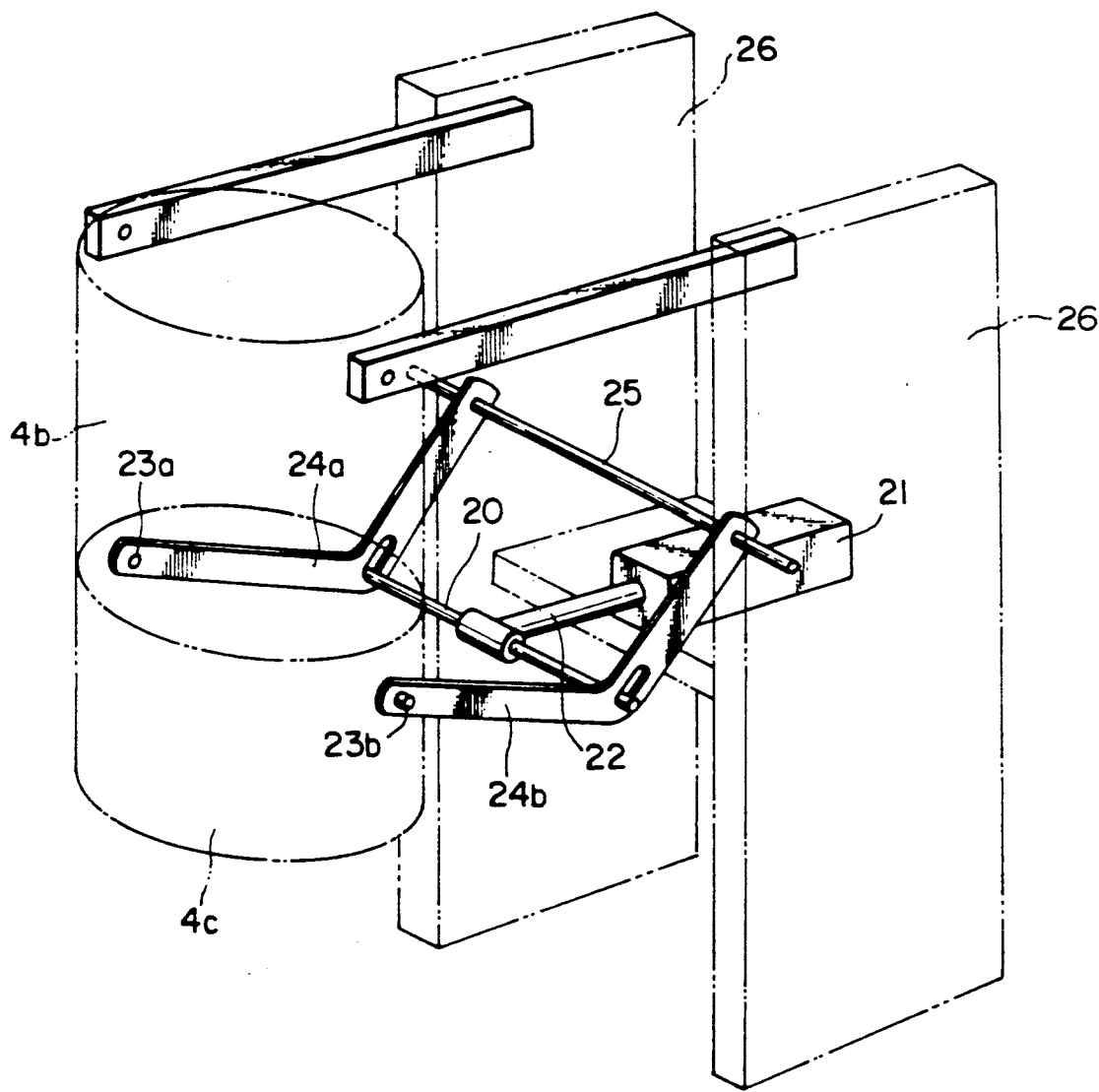
FIG. 4A is perspective view showing a mechanism to detach the bottom portion of the culture apparatus according to the present invention.
Figure 4B:
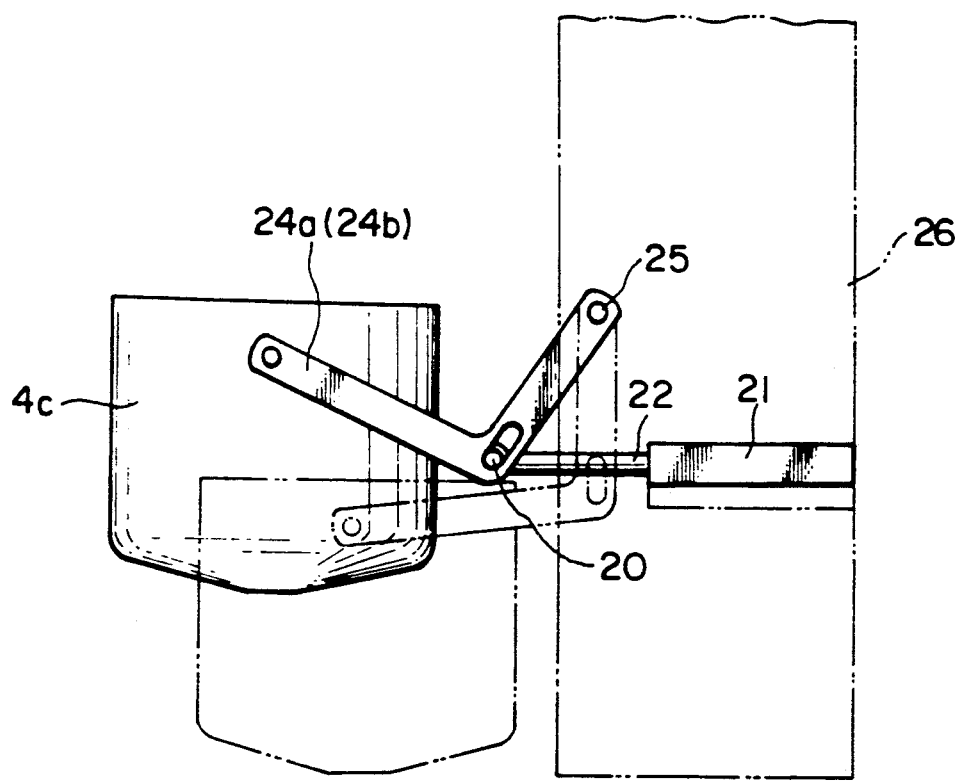
FIG. 4B is diagram illustrating a manner in which the detaching mechanism operates.

Now a mechanism for removal of immobilizing carriers from the culture tank 4 will be explained by way of example in reference with FIGS. 4A and 4B.

The lower portion 4c of the culture tank 4 is separable from the intermediate drum-like portion 4b by means of a link mechanism and a cylinder, as will be described later more in details. Specifically the drum-like portion 4b is supported on stands 26 through links 24a, 24b mounted on the stands 26 at an intermediate level. Reference numeral 25 designates a supporting shaft by which the links 24a and 24b are pivotally supported by the stands 26 and the links 24a and 24b are interconnected by a tie rod 20 at respective angular portions of said links 24a, 24b. The lower portion 4c of the culture tank is pivotally lowered around the shaft 25 as said tie rod 20 is pulled by a piston rod 22 associated with a cylinder 21, and thereby the lower portion 4c is separated from the drum-like portion 4b of the culture tank 4. The links 24a, 24b are pivotally mounted at respective front ends to the lower portion 4c of the culture tank 4, so that the lower portion 4c can be maintained in a horizontal condition as shown by FIG. 4B, facilitating removal of the immobilizing carriers out from the culture tank 4.

As will be apparent from the foregoing description, the cell culture apparatus is advantageous in that the lower portion thereof is separable and thereby removal of the immobilizing carriers out from the apparatus is facilitated.

While there has been described what is at present considered to be preferred embodiment of the invention, it will be understood that various modifications may be made therein, and it is intended to cover in the appended claims all such modifications as fall within the true spirit and scope of the invention.

What is claimed is:

1. A method for cell cultivation comprising the steps of:
   (1) proliferating adhesive cells in a culture medium contained in a small preliminary culture tank having immobilizing carriers therein;
   (2) stripping the proliferated cells from the carrier;
   (3) mixing the stripped cells with culture medium to form a cell suspension;
   (4) collecting the cell suspension in an intermediate reservoir and retaining the cell suspension therein until the cells are uniformly distributed in said suspension; and
   (5) intermittently transferring the suspension into a main culture tank containing immobilizing carriers comprising a ceramic material as a the major ingredient thereof and allowing the cells to adhere thereto for further cultivation of the cells.

2. Method as recited by claim 1, wherein the carrier of the small preliminary culture tank is a microcarrier.

3. Method as recited by claim 1, wherein said cell suspension is supplied to the main culture tank simultaneously from top and bottom thereof so that the cells uniformly adhere to said immobilizing carriers.

4. Apparatus for cell culture comprising a preliminary culture tank of a small size containing immobilizing carriers a main culture tank filled with immobilizing carriers comprising a ceramic material as a major ingredient, and an intermediate reservoir interposed between said preliminary culture tank and said main culture tank, said intermediate reservoir having means to circulate culture medium into said preliminary culture tank and, after cell proliferation, to supply a quantity of cell suspension to said main culture tank.

5. Apparatus as recited by claim 4, wherein a culture medium adjusting tank is connected to the main culture tank and has means to adjust nutrient and gas content in the culture medium and to circulate the culture medium within said main tank.

6. Apparatus as recited by claim 4, wherein the carrier in the preliminary culture tank is a microcarrier.

7. Apparatus for cell culture of adhesive cells for the production of a target substance, said culture apparatus comprising a culture tank having immobilizing carriers therein, an inversed funnel-shaped inlet for the tank located above the carriers and a perforated plate attached to the bottom of said inlet for uniform distribution of a quantity of cell suspension supplied to the tank from above the carriers, a plate in the form of a net located immediately under the carriers to support the carriers, and another perforated plate located under the plate in the form of a net for uniform distribution of another quantity of cell suspension supplied to the tank from beneath the carriers.

8. Apparatus as recited in claim 7, wherein said culture tank further comprises an upper lid adapted for detachably carrying the inversed funnel-shaped fluid inlet, an intermediate drum-shaped portion fixed to a stand and being detachably connected to said lid, and a lower portion adapted for detachably carrying the plate in the form of a net and being detachably connected to said drum-shaped portion.

9. Apparatus as recited by claim 8, wherein the detachable lower portion is held on or detachable from the drum-shaped portion by means of a link mechanism and a cylinder.

10. Apparatus as recited by claim 9, wherein the link mechanism is capable of lowering the lower portion to detach it from the drum-shaped portion.

* * * * *